United States Patent
Kantrowitz et al.

(10) Patent No.: US 6,199,233 B1
(45) Date of Patent: *Mar. 13, 2001

(54) RADIOLUCENT TABLE EXTENSION ASSEMBLY

(76) Inventors: Allen Kantrowitz, 5170 Pine Tree Dr.; In Ki Mun, 4045 Sherida Ave., #263, both of Miami Beach, FL (US) 33140; Charles E. Dinkler, 524 Hamblin Dr., Cincinnati, OH (US) 45255

(*) Notice: Subject to any disclaimer, the term of this patent is extended or adjusted under 35 U.S.C. 154(b) by 0 days.

This patent is subject to a terminal disclaimer.

(21) Appl. No.: 09/517,644

(22) Filed: Mar. 3, 2000

Related U.S. Application Data

(63) Continuation of application No. PCT/US98/18405, filed on Sep. 3, 1998
(60) Provisional application No. 60/083,014, filed on Apr. 24, 1998.

(51) Int. Cl.[7] .............................. A61G 13/12; A47C 20/02
(52) U.S. Cl. ......................... 5/601; 5/622; 5/632; 5/638
(58) Field of Search .............................. 5/601, 621, 622, 5/632, 638, 640, 643; 248/220.21, 220.22, 224.51

(56) References Cited

U.S. PATENT DOCUMENTS

| | | | |
|---|---|---|---|
| 4,506,872 | * 3/1985 | Westerberg et al. | 5/601 |
| 4,616,814 | * 10/1986 | Harwood-Nash et al. | 5/601 |
| 4,688,780 | * 8/1987 | Hanz | 5/601 X |
| 5,276,927 | * 1/1994 | Day | 5/601 X |
| 5,335,384 | * 8/1994 | Foster et al. | 5/622 |
| 5,560,728 | * 10/1996 | McFadden | 5/637 X |
| 5,675,851 | * 10/1997 | Feathers | 5/601 X |
| 5,771,512 | * 6/1998 | Kurakake et al. | 5/621 X |
| 5,911,655 | * 6/1999 | Brenneisen | 5/601 X |
| 6,003,174 | * 12/1999 | Kantrowitz et al. | 5/601 |
| 6,042,184 | * 3/2000 | Kofoed | 5/638 X |
| 6,049,926 | * 4/2000 | Amaral | 5/622 |
| 6,081,947 | * 7/2000 | Disher | 5/632 |
| 6,138,302 | * 10/2000 | Sashin et al. | 5/601 X |

* cited by examiner

*Primary Examiner*—Terry Lee Melius
*Assistant Examiner*—Robert G. Santos
(74) *Attorney, Agent, or Firm*—Wood, Herron & Evans L.L.P.

(57) ABSTRACT

An elongated patient support table [22] with a horizontal patient support surface has a contoured radiolucent table extension assembly [26, 126] connected thereto in cantilever fashion for supporting the head and upper torso of a patient [27]. An outer end of the extension assembly [26, 126] has a reduced width compared to the support table [22] to enable extendable movement of the radiolucent extension assembly [26, 126] into a scanning zone defined by a central opening [112] of a diagnostic unit such as a CT scanner [20]. The table extension assembly [26, 126] supports the patient [27] via an inboard radiolucent horseshoe headrest [32, 132] and an outer tool support [54, 122] for holding an outer stabilization device [66, 166] such as a radiolucent skull clamp [74, 174]. The combination of the support table [22] with the radiolucent table extension assembly [26, 126] and the inner and outer stabilization devices [32, 132, 66, 166] support the patient [27] in a desired position during successive scanning or surgical procedures. With an imaging system [24] operatively connected to the CT scanner [20], the table extension assembly [26, 126] permits a neurosurgeon to conveniently obtain updated images of the scanned region after performing a stereotactic operative procedure, thereby to immediately and easily determine if any follow-up procedures are necessary before closing up the surgical incision.

13 Claims, 6 Drawing Sheets

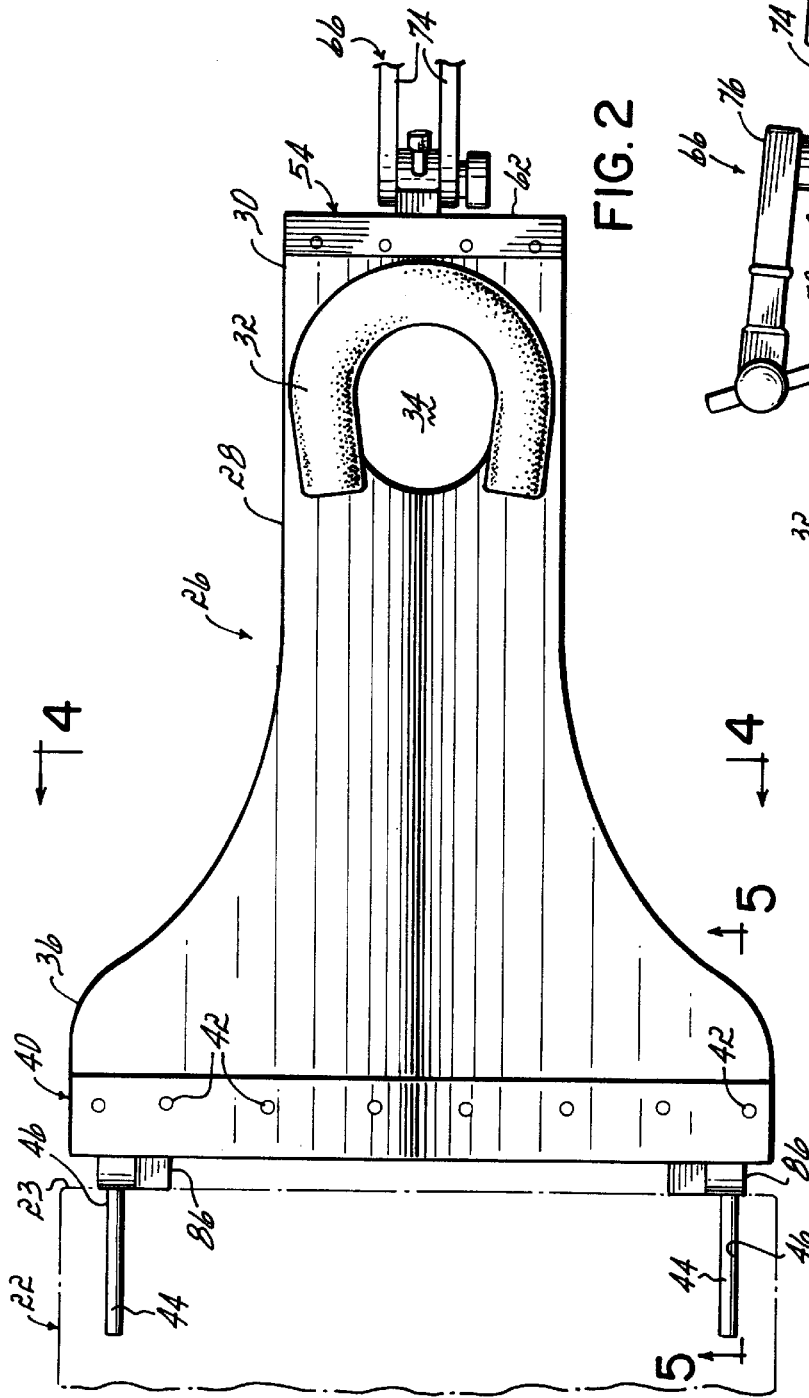
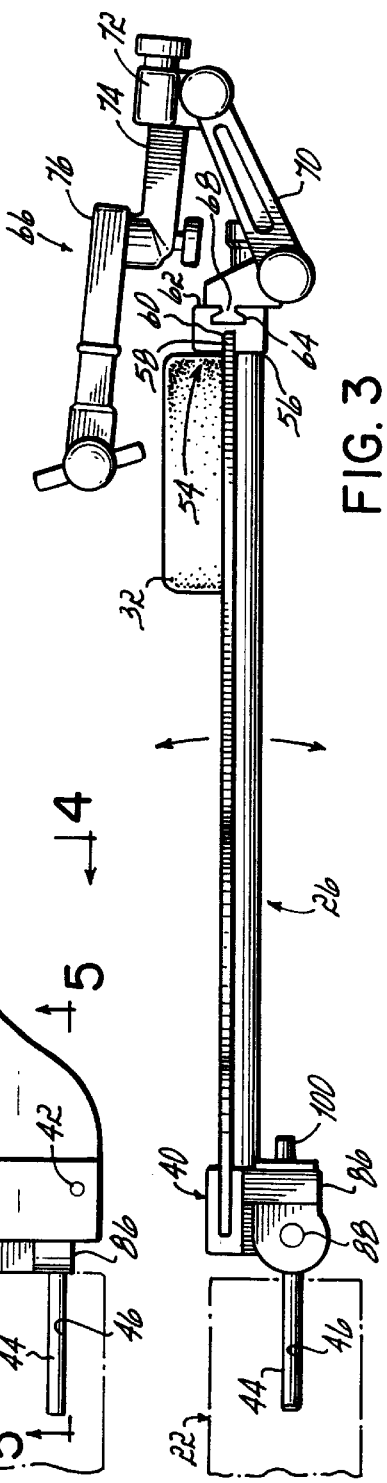

RADIOLUCENT TABLE EXTENSION ASSEMBLY

This application is a continuation of PCT application Ser. No. PCT/US98/18405, entitled "Radiolucent Table Extension And Method," filed on Sep. 3, 1998, which in turn claims priority to U.S. application Ser. No. 08/922,969, filed on Sep. 3, 1997, and issued on Dec. 5, 1999 as U.S. Pat. No. 6,003,174, and U.S. Provisional Application Serial No. 60/083,014, filed on Apr. 24, 1998.

FIELD OF THE INVENTION

This invention relates to beds and more particularly, to an improved surgical operating table.

BACKGROUND OF THE INVENTION

With current medical practices, it is common for a patient to undergo a diagnostic scanning procedure, which is normally performed in a separate suite containing the scanning machine and dedicated to scanning procedures. The scanning machine may be a CT, MRI, or other scanning device. Thereafter, the scan data is utilized in a surgical planning process, which conventionally takes place at a location, for example, an office or an operating room. In some surgical procedures, the scanning data is utilized with a system for post processing the scan data acquired during imaging. Further, the imaging system may be located in a surgical suite, and the surgical planning performed before and during surgical procedure utilizing the imaging system and scan data.

During the scanning procedure, the patient must maintain a perfectly still and motionless posture, and while most often, the patient simply lies on a scanning support table, in some situations, the patient may be supported in the desired scanning position with pads, straps or other supports. Further, the support on which the patient rests is normally radiolucent, that is, transparent to the scanning device, so that the support does not compromise the utility of the scanned image. Further, the patient support used for scanning normally translates with respect to the imaging device. Translation of the patient support permits the patient to be moved into the scanning field or zone of the scanning machine.

After the scanning process is completed, often the patient is then moved to an operating room which requires either that the patient walk, or be carried, for example, by transferring the patient from the scanning table to an operating table. Alternatively, as illustrated in U.S. Pat. No. 5,475,884, the patient may be supported on a portable support plate, which is easily moved between the scanning table and the operating table. The scan data is often used in a post processing imaging system for surgical planning purposes both prior to and during surgery. If during or after a surgical process, it is desired to scan a patient again, the patient must be moved from the operating room to the scanning suite, transferred to and from the operating table to the scanning table, and after scanning, transferred back to the operating table and returned to the operating room. The above process is cumbersome, time consuming and potentially risky for the patient.

Some newer scanning machines are substantially reduced in size. One such machine is shown in FIGS. 2 and 3 of U.S. Pat. No. 5,499,415, which show an annular-shaped scanner mounted on a wheel-supported frame, to enable the scanner to be used at multiple sites. Consequently, such scanning machines do not require their own suite or room, but instead, they may be used within the operating suite itself. Thus, in an operating room, the patient may be scanned; the surgical planning performed; an operative procedure executed; and the patient scanned again to determine the current status of the operative procedure. Based on the new scanned images, the operative procedure can be continued and the above process repeated as necessary.

A limitation of the current state-of-the-art is that the posture of the patient during the scanning process is often different from the patient's posture during surgery. If a patient is positioned in one posture on a scanning table during the scanning process, and then is moved to an operating table, that motion of the patient may cause the position of the target to change with respect to the body surface. During surgery, this problem is compounded by tissue shifts attendant to the opening of body cavities, removal of body fluid or tissues and tissue retractions. Thus, while such motion may be small, any motion of the target will reduce or compromise the utility of the preoperative scan data.

The solution to these problems is to scan the patient in the operating room during surgery while the patient is maintained in the surgical posture.

While current scanning tables are radiolucent and provide a translation to move the patient into the scanning machine, such scanning tables do not have the accessories required to attach, support and stabilize surgical instrumentation and to properly support the patient's body in the desired surgical posture. Further, while operating tables contain numerous accessories and couplings to which surgical instrumentation may be attached and supported, most operating tables are not compatible with scanning instrumentation. Thus, as presently known, scanning tables cannot be used as operating tables, and generally, operating tables are inappropriate for use as scanning tables.

It is an object of this invention to overcome the above-described limitations in the prior art, by facilitating the function of supporting a patient in a desired position in a manner which readily accommodates successive surgical or scanning procedures.

SUMMARY OF THE INVENTION

The present invention achieves the above-stated objective with a radiolucent table extension that connects to a surgical table and permits a patient to be positioned on the table in a posture suitable for successive surgical or scanning procedures, with the head and the upper torso of the patient supported on the table extension and the radiolucent table extension including additional cooperative components such as a radiolucent horseshoe headrest and a radiolucent skull clamp to positively hold the patient relative to extension. The radiolucent table extension is cantilevered from one end of the surgical table and it is shaped so that it may be moved in a relative manner into a toroidal shaped scanning zone of an upright annular scanning machine. This permits the patient to be scanned in the desired surgical posture. This radiolucent table extension is especially useful for those procedures in which it is desirable to maintain the patient in a desired position during successive scanning or surgical procedures.

By operatively connecting the toroidal scanner to an imaging system, so that the imaging system may store data representative of scans of the patient taken in the scanning zone, and by supporting the patient with the extension and fixing the position of the patient with the horseshoe headrest and the skull clamp, this invention facilitates the positioning of the patient during successive scans, thereby assuring the accuracy of the scanned data. This helps the surgeon to know almost immediately whether the surgical procedure accomplished its objective, or whether a subsequent surgical procedure may be necessary.

According to the principles of the present invention and in accordance with the preferred embodiments, a radiolucent table extension has a first end adapted to be attached to one end of a table. The table extension includes a contoured radiolucent member designed to support an upper torso and head of a patient with the rest of the patient's body being further supported by an adjacently located surface of the table. The member has a sufficiently narrow width to permit it to be extended, in cantilever fashion, into a scanning zone of portable CT scanning system. A tool support extends along a periphery of the member and is designed to receive and support at least one outboard stabilization device, such as a skull clamp, to positively hold the patient in a fixed position relative to the member. The extension also includes at least one inboard stabilization device. More specifically, inboard of the periphery a radiolucent horseshoe headrest also provides stabilized support for the patient. Therefore, the patient can be supported on the radiolucent table extension in the desired posture. The patient can then be conveniently scanned before a surgical procedure. After surgery, a subsequent scanning procedures may be performed if necessary or desired. Thus, the table extension has the advantage of not requiring that the patient be moved with respect to the table extension between successive scanning and surgical procedures.

Moreover, with updated scanned images readily available for viewing via the imaging system, the surgeon can review the results of a surgical procedure to determine if a particular operation has been completely successful. For example, if the objective of the surgery was to completely remove a hematoma from the brain, a follow-up scan may enable the surgeon to use the imaging system to determine if the entire hematoma has been removed. If a subsequent scan shows that some of the "target" remains, then the surgeon can perform another surgical procedure, using the imaging system if desired, to achieve 100% removal of the target. Thus, this overall system facilitates successive scanning and surgical procedures, and the table extension assembly makes it possible to use this system more effectively, by assuring accurate and repeatable positioning of the patient.

In one aspect of the invention, a hinge mechanism mechanically couples the radiolucent member to an operating table, thereby permitting the table extension to be pivoted or rotated with respect to the table. Thus, the patient's head and upper torso may be raised or lowered and supported in any desired position to facilitate the scanning and operative procedures.

In a further aspect of the invention, the tool support extends along the periphery at one end of the table, but in another aspect of the invention, the tool support extends along the periphery including the lateral edges of the table. Thus, a wide variety of surgical instruments may be connected to the table extension to facilitate many different surgical procedures.

In still another aspect of the invention, the table extension includes a radiolucent horseshoe headrest removably mounted to the radiolucent member, inboard of the peripheral edge, and it is tiltable with respect to the member. This horseshoe headrest may surround a portion of an opening in the member, when viewed from above. The removable, tiltable horseshoe headrest optimizes versatility for the neurosurgeon in positioning a patient.

If desired, the tool support may be detachable from an external edge of the member. This enables a surgical drape, shaped in a bag-like form, to extend over the head of an intubated patient stabilized in position by the radiolucent horseshoe headrest. The headrest resides "inboard" of the peripheral edge with the patients' head and upper torso supported relative to the member.

Thereafter, the tool support can be connected to the edge of the member, with the drape sandwiched therebetween, and the skull clamp attached "outboard" to the tool support. This places the tooling connected to the tool support, i.e., the skull clamp, within the sterile field. This arrangement represents an advantageous option for some types of surgical and/or scanning procedures. For one thing, the drape is more closely confined to the table extension so that the surgeon and other hospital attendants can readily determine visually that the table extension and the patient can be extended within the scanning zone of the scanner without impediment. For some procedures, this arrangement also simplifies connection of the skull clamp.

These and other objects and advantages of the present invention will become more readily apparent during the following detailed description taken in conjunction with the drawings herein.

BRIEF DESCRIPTION OF THE DRAWINGS

FIG. 2 is a top plan view of the radiolucent table extension assembly of FIG. 1.

FIG. 3 is a side view in elevation of the radiolucent table extension assembly of FIG. 1.

DETAILED DESCRIPTION OF THE INVENTION

Figure 1:
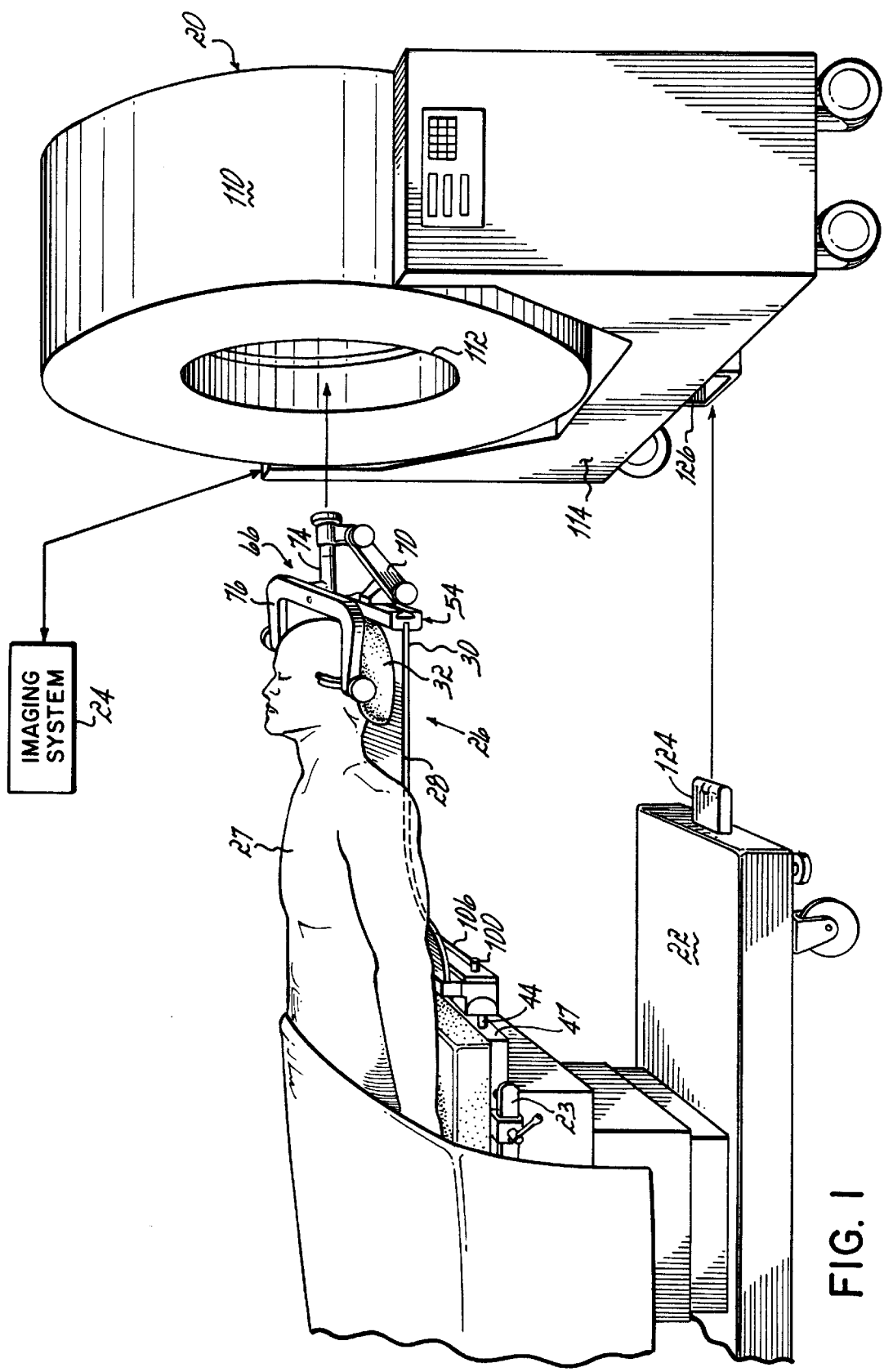
FIG. 1 is a perspective view of a portion of an operating table including a radiolucent table extension assembly in accordance with the principles of the present invention.

Referring to FIG. 1, a portable CT scanning system 20 is located in an operating suite with an operating table 22. The CT scanning system may be either a mobile system such as that commercially available from Analogic of Peabody, Massachusetts or a stationary scanning system such as that commercially available from General Electric Medical Systems of Milwaukee, Wisconsin. The operating table 22 may be one of many commercially available tables, for example, an operating table commercially available from Amsco of Erie, Pa., MDT Diagnostic Co. of N. Charleston, N.C., or other suppliers. The operating table has a lateral rail 23 extending along each side of the table to which retractors, clamps and other devices may be attached and stably supported. A stereotactic image processing system 24, for example, the MAYFIELD-ACCISS image processing system, commercially available from Ohio Medical Instrument Company, Inc. of Cincinnati, Ohio is operatively connected to the scanner 20 and responsive to scan data provided by the CT system 20, to provide selected images on a display screen of the scan data along selected planes. To facilitate the use of the operating table 22 with the CT system 20, one end of the operating table is used to support a radiolucent table extension, or table extension assembly, 26 in accordance with the present invention. Use of an imaging system 24 of this type is described in U.S. Pat. No. 5,695,501, which is expressly incorporated by reference herein, in its entirety.

Figure 4:
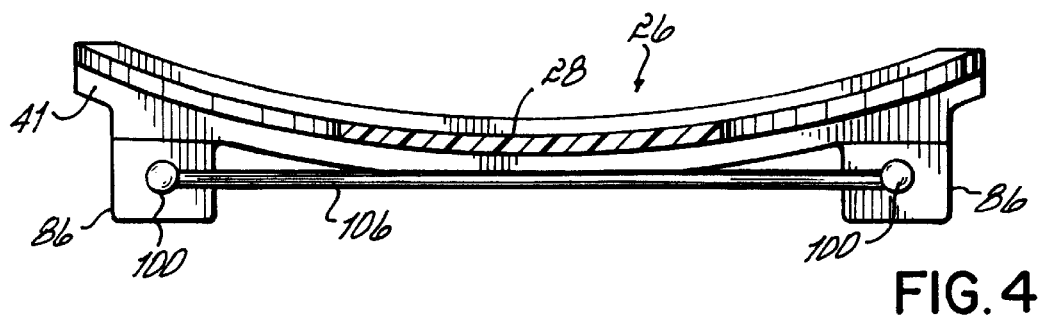
FIG. 4 is a cross-section view taken along the line 4—4 of FIG. 2.

Referring to FIG. 2, the table extension 26 includes a support member or plate 28 made of radiolucent material, for example, wood, carbon graphite, etc, and the table extension 26 has a length to normally support the upper torso and head of a patient 27, the upper torso being defined as the portion of the patient's body above the waist including the head. As shown in FIG. 4, the patient support member 28 has a curved cross-sectional profile and has a laminated construction with a center layer of mahogany between two outer layers of carbon graphite, although the invention also contemplates molding the member 26 as one integral piece. The curve is normally a circular arc having a relatively large radius, for example, 28 inches, to generally conform to the shape of a patient. The support member 28 may have a length up to about 52 inches, although most procedures can be accommodated with a shorter-length, such as 36 inches. The outer or distal end 30 of the support member 28 includes a horseshoe headrest 32 that is generally U-shaped and filled with a gel to comfortably and properly support the patient's head. The headrest 32 surrounds an opening 34 within the support member 28. The opening 34 is sized to receive the face of a patient lying on the support member 28 in a prone position. The distal end 30 is narrower than the inner or fixed end 36, and the narrow profile of the distal end 30 of the support plate 28 facilitates positioning the distal end 30 in scanner 20 even if the table or the scanner 20 is tilted. The support member 28, when viewed from the top as shown in FIG. 2, has a profile that flares outward from the distal end 30 to the fixed end 36. The width of the support member 28 at the fixed end 36 is generally greater than the distance between the holes 46 and is normally equal to the width of the operating table 22.

Figure 5:
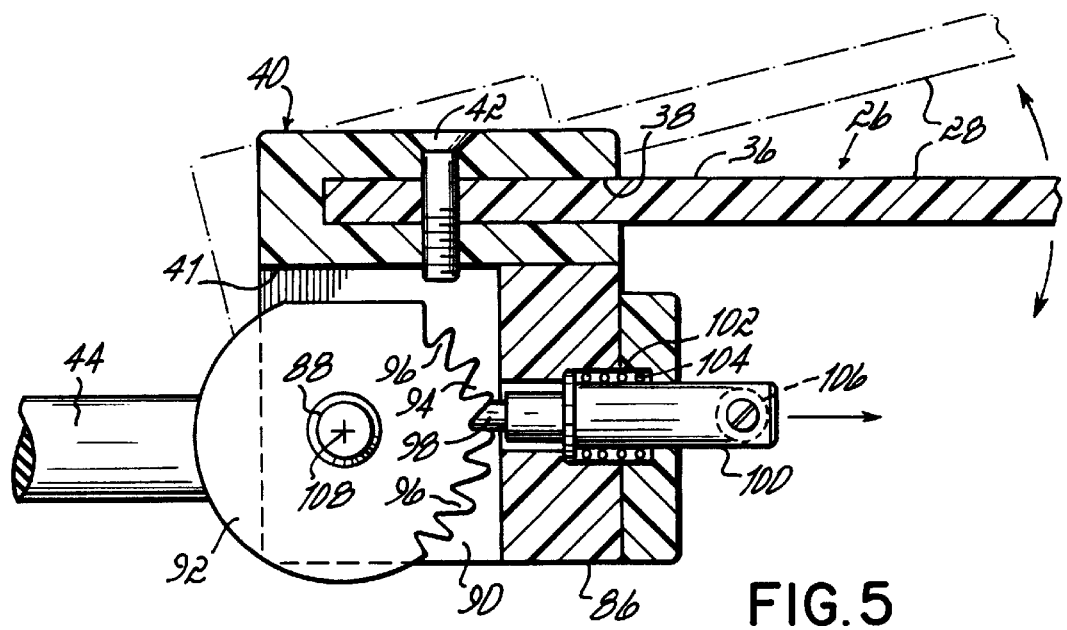
FIG. 5 is a cross-section of view taken along the line 5—5 of FIG. 2.

Referring to FIG. 5, the support member 28 is secured at its fixed end 36 within a slot 38 of an attachment base 40. Fasteners, for example, screws 42 are used to clamp and secure the support plate 28 within the attachment base 40. The attachment base 40 is mechanically linked to support shafts 44, which extend longitudinally from the fixed end of the support base 40 and are sized to fit into holes 46 of the table 22. Thus, the support plate 28 provides an extension of and is cantilevered from the end 23 of the table 22.

Referring to FIGS. 1–3, an instrument or tool support or rail 54 is attached to the periphery of the distal end 30 of the support plate 28. The tool support 54 may be made from a "DELRIN®" acetal polymer material, a polyethersuylfone ("PES") material or a carbon graphite. An inner directed side 56 of the tool support 54 includes a slot 58 for receiving the portion of the periphery 60 of the support plate 28. The support plate 28 may be secured in the slot 58 using fasteners or adhesives or both. The slot 58 is curved with respect to a radius sweeping a vertical plane that is generally perpendicular to and extends across the width of the support plate 28. An outer directed side 62 of the tool support 54 includes a second slot 64 that is generally parallel to a longitudinal center line of the tool support 54. Thus, when viewed from the end of the support plate 28, that is, looking to the left in FIG. 3, the slot 64 will appear generally as a straight slot. The slot 64 permits medical instruments, such as stabilization devices 66, for example a skull clamp, retractors, clamps, supports, etc., also collectively referred to as "tools" herein, to be supported, selectively moved with respect to the distal end 30 of the support plate 28 to desired positions and locked or secured in place. In the illustrated embodiment, the slot 64 has a dovetail shape that matches a mating dovetail on the tool to be mounted and secured to the tool support 54. For example, the tool support 54 may receive one end 68 of a transitional element 70. The other end 72 of the transitional element 70 is rotatably coupled to a swivel adapter 74. The swivel adapter, in turn, is coupled to a skull clamp 76. The skull clamp 76 is normally manufactured from radiolucent materials, for example, as described in U.S. Pat. No. 5,276,927 issued to the assignee of the present invention.

As shown in FIG. 3, the support plate 28 is often used in a generally horizontal position such that the top of the operating table 22 is generally in line with the support plate 28. However, numerous surgical procedures require that the support plate 28 be tilted or pivoted up or down with respect to the end 25 of the table 22. The tilting or pivoting of the support plate 28 is accomplished by the mechanism illustrated in FIG. 5. The attachment base 40 includes a pair of housings 86 connected to a lower surface 41 at a location near the ends of the attachment base 40 (FIG. 4). The attachment base 40 and housings 86 may be cast or made from aluminum. The support shafts 44 are rigidly connected at one end to respective cross-shafts 88 that are rotatably mounted within the lateral side walls 90 of the housings 86. The cross-shafts 88 extend through brass bushings (not shown) mounted in the lateral side walls 90 and function as pivot pin in a hinge. The support shafts 44 function as fixed hinge members, and the housings function as movable hinge members. A ratchet wheel 92 is fixed at the center of each of the cross-shafts 88, and each ratchet wheel has notches 94 between teeth 96. The support shafts 44, crossshafts 88, and ratchet wheels 92 are normally made from stainless steel.

Pawls 98 are shaped to mate with and fit into the notches 94 of respective ratchet wheels 92. Each pawl 98 is mounted on the end of a release shaft 100 that extends through a bore 102 of a respective housing 86. With the pawls 98 in the position illustrated in FIG. 5, they function to securely support their respective housings 86 and the support plate 28 in a generally horizontal position. A spring 104 provides a bias to forcibly maintain the pawls 98 within the slots 94. The pawls 98 and release shafts 100 are normally made of stainless steel.

As shown in FIG. 4, a release shaft or bar 106, normally made of aluminum or stainless steel, extends between the shafts 100 and the housings 86. By pulling on the bar 106, the shafts 100 move to the right as viewed in FIG. 5; and the pawls 98 are pulled out of engagement with respective ratchet notches 94. Once the pawls 98 are disengaged from the notches 94, the support plate 28, attachment base 40, and housings 86 are freely rotatable relative to respective stationary ratchet wheels 92, cross-shafts 88 and support shafts 44. Thus, the support plate 28 may be pivoted with respect to an axis of rotation 108 in the generally clockwise or counter-clockwise direction until the support plate 28 is at its desired angular position as shown in phantom in FIG. 5. Normally, the support plate 28 may be pivoted approximately 60° above and below its illustrated horizontal position. When the bar 106 is released, the springs 104 push their respective pawls 98 into the closest ratchet notches 94, thereby securing the support plate with the desired angle or tilt.

In use, referring to FIG. 1, the scanning system 20 and operating table 22 are brought into a surgical suite. The scanning system 20 has a toroid shape scanning element 110 with a central opening 112 defining an enclosed or encircled scanning zone with which the portion of the patient to be scanned is axially aligned. The scanning element 110 further has the capability of rotating or tilting within its base 114 with respect to a diametric horizontal axis. The distal end 30 of the support plate 28 is narrowed so that it can extend into the opening 112 without interference. If necessary, the head section (not shown) of the table 22 is removed therefrom, and the radiolucent table extension 26 is mounted to the table by inserting the support bars 44 into mating bores 46 on the end surface 47 of the table 22. The patient 116 is then positioned on the table in a posture suitable for a surgical procedure. The length of the support plate 28 is sized such that the patient's upper torso and head are accessible for scanning and surgical procedures. The portion of the patient's anatomy on which the surgical procedure is to be performed may be stabilized by various clamps and restraining devices, for example, the skull clamp 76. Further, the support plate 28 or the scanning element 110 may be tilted so that the desired posture and/or scanning plane is achieved.

When the desired surgical posture is achieved, normally the patient will have already been scanned; and the surgical planning and procedure can be performed. Thereafter, a portion of the radiolucent table extension 26 is then moved into the opening 112, for a follow-up scan. The extent to which the extension 26 is moved into the opening 112 depends on what portion of the head or upper torso is to be scanned. The initial alignment of the table extension may be determined by visual inspection; and thereafter, a scan made to determine exactly whether and to what extent the table extension may be out of alignment. Alternatively, the scanner may be equipped with LED's or other sources of light providing beams of light with which the table extension can be aligned. In another embodiment, the table 22 may have an alignment tab 124 (FIG. 1) which is moved into an alignment slot 126 on the scanner 110. When the tab 124 is properly seated in the slot 126, the table is properly aligned with the scanner 110. The scanning process is executed by the scanning machine moving the scanning element 110 incrementally in an axial direction and with each increment, a scan is taken. Thereafter, the extension 26 and the patient are removed from within the scanning element 110, either by moving the scanning machine 20 or the operating table 22. The scan data is then used in association with the imaging systems 24 to plan the surgical procedure. The surgical procedure is then performed, and thereafter, the patient may be moved back into the scanning machine 20, and the scanning process repeated. The scanning and imaging system may be used to gauge the effectiveness of the surgical procedure; and if necessary, further procedures performed. The above process may be executed any number of times with the patient remaining in the desired position on the same patient support.

Thus, the above-described operating table and radiolucent table extension has a significant advantage of not only being able to support a patient during a scanning process, but also support the patient in the identical posture during a surgical procedure. The radiolucent table extension permits an operating table that is normally nonradiolucent and inappropriate for scanning purposes to be used with a scanning machine. Further, the table extension may be tilted to accommodate different desired surgical postures and is sized and shaped to readily fit within the opening of a scanning element, whether in a horizontal or tilted position. Further, not only does the table position permit successive scanning and operative procedures on the upper torso and head of a patient, but the radiolucent table extension 26 readily supports the patient in a prone, or supine position.

Figure 6:
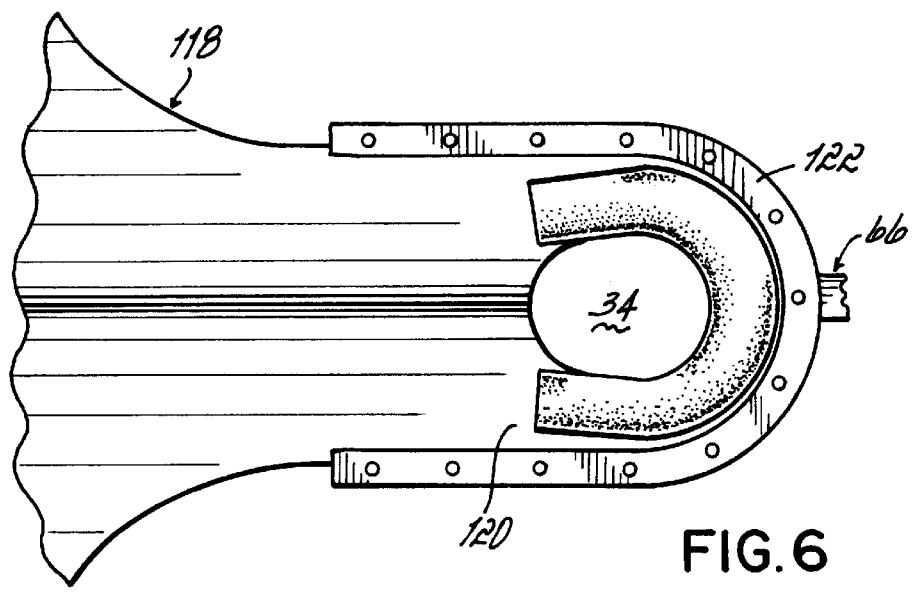
FIG. 6 is a top plan view of an alternative embodiment of the radiolucent table extension assembly in accordance with the principles of the present invention.
Figure 7:
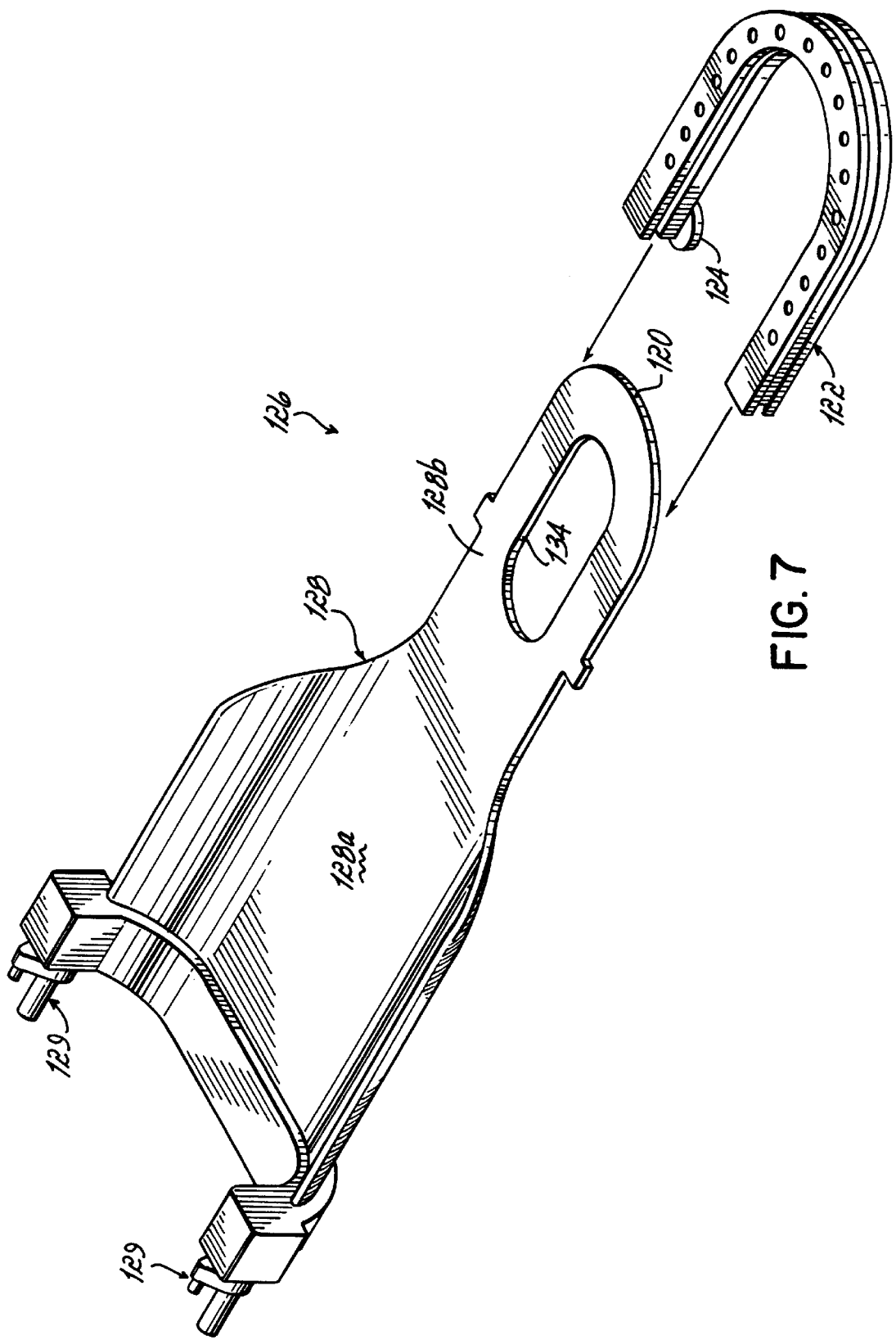
FIG. 7 is a perspective view of yet another alternative embodiment of a table extension assembly in accordance with the present invention.

Referring to FIG. 6, an alternative embodiment of the support plate 118 has an distal end 120 that is curved to generally follow the profile of the headrest 32. Further a tool support 122 extends along the periphery of the support plate 118 to a location at which the width of the support plate 118 begins to flare outwardly toward the width of the fixed end 32. Other than its length, the construction and function of the tool support 122 is substantially identical to the tool support 54 described earlier.

Figure 8:
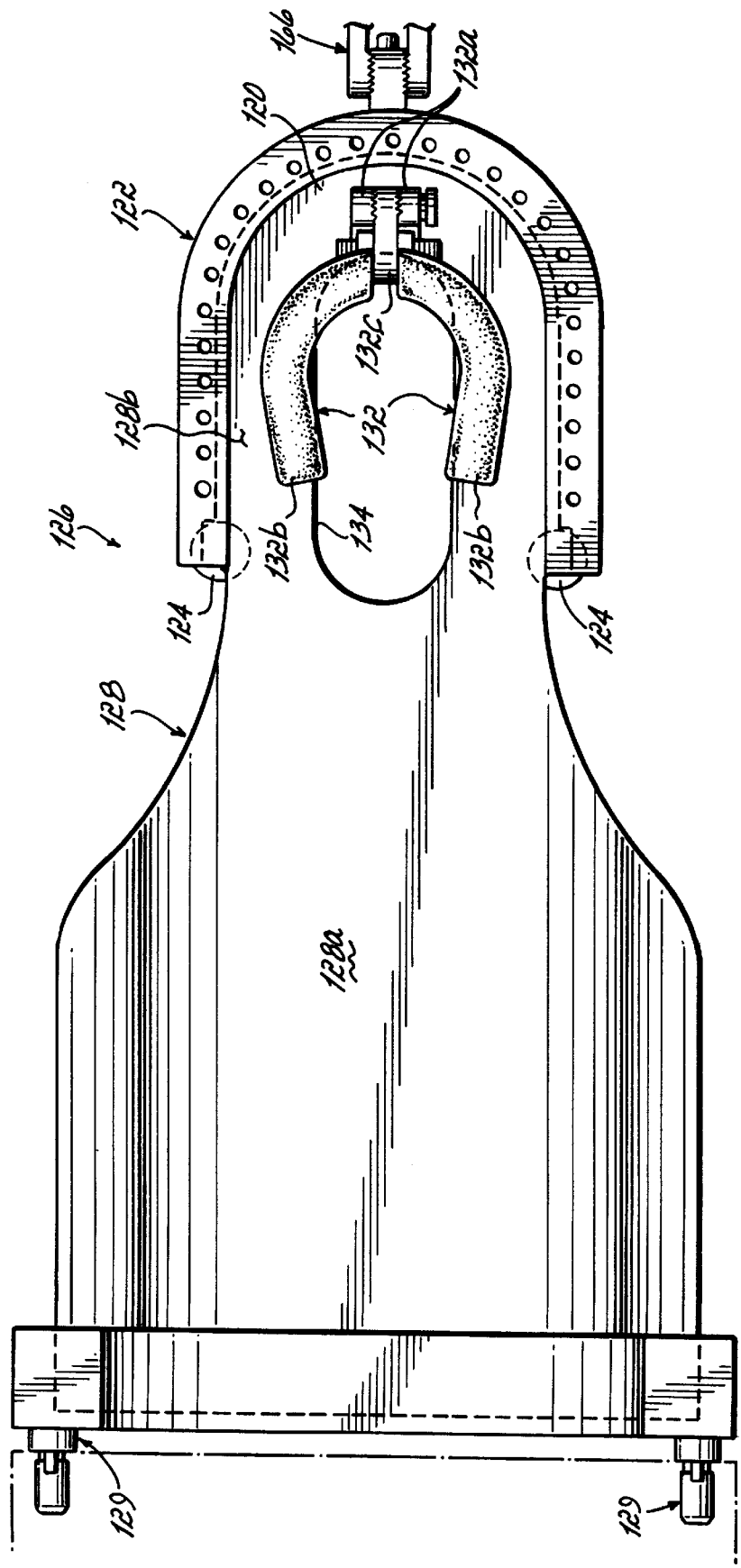
FIG. 8 is a top plan view of the table extension assembly shown in FIG. 7, but with additional hardware shown, namely an inboard horseshoe headrest.
Figure 9:
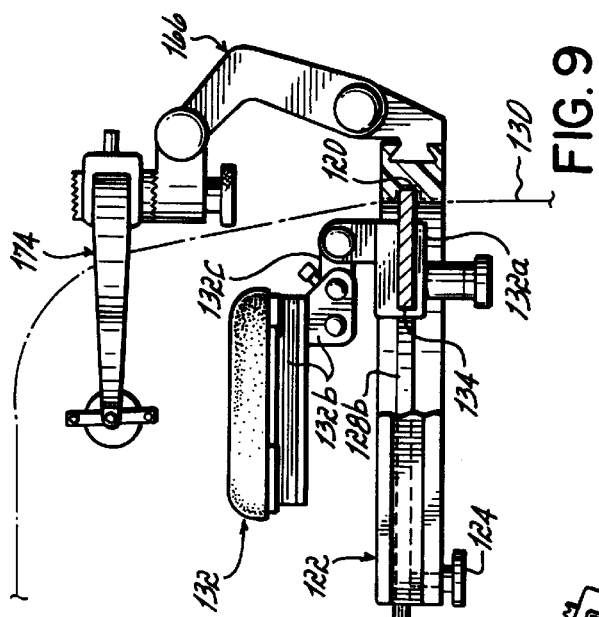
FIG. 9 is a side view of the table extension of FIG. 8, but also showing an outboard stabilization device, in this case a skull clamp, secured to the tooling support outboard of the edge of the table extension.
Figure 10:
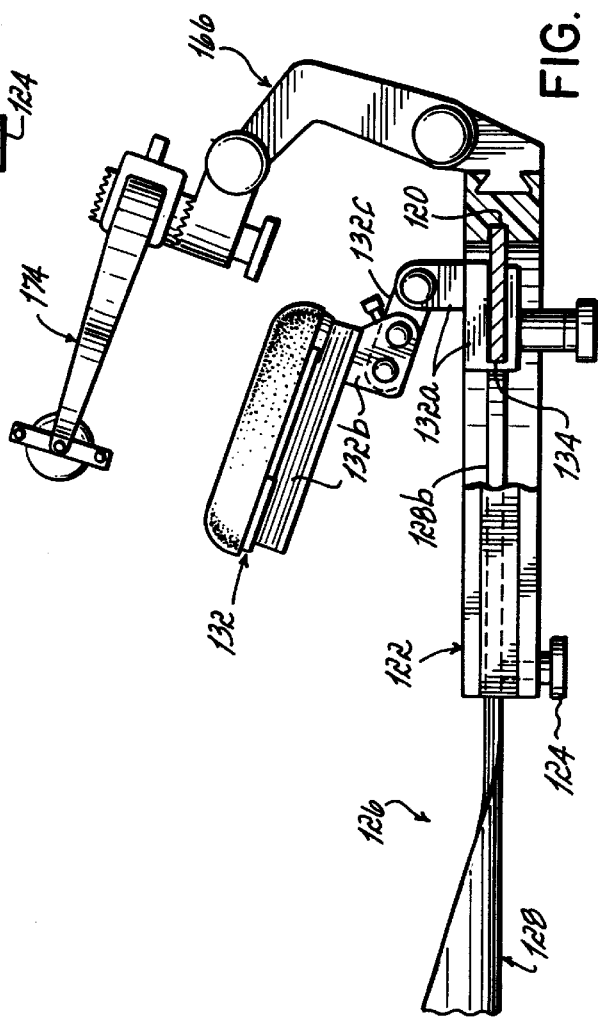
FIG. 10 is a side view, similar to FIG. 9, showing the inboard horseshoe headrest tilted relative to the table extension assembly.

According to a further variation of this embodiment, as shown in FIGS. 7–10, a radiolucent table extension assembly 126 includes a tool support 122 removably connected to the peripheral edge at a distal end 120 of the support member 128. The support member 128 is preferably pivotal relative to a table (not shown) to which is connected. This is done by incorporating a pivot mechanism (not shown) into the table extension assembly 126 or even into the table itself, as with surgical tables commercially available from Midmark of Dayton, Ohio, which are built so as to tilt relative to horizontal. With such tube, the support member 128 is simply plugged via pins 129 into the table (not shown) which is already oriented at a desired angle. The support member 128 may have an inner portion 128a which is contoured to the body of the patient and an outer portion 118b which is generally flat. The tool support 122 may removably secure to the support plate 128 via a pair of hand-tightenable knobs 124. The member 128 includes an opening 134, and a radiolucent horseshoe headrest 32 or 132 resides inboard of, and generally in alignment with, a portion of the opening 134 as shown in FIGS. 8–10. This configuration enables a baglike surgical drape (not shown) to be placed over a patient who is supported on the support member 128 by the horseshoe 132, and in an intubated condition, and then the tool support 122 connected to the distal end 120 to confine the drape within the edge of the support member 128, between the support member 128 and the tool support 122. Phantom line 130 in FIG. 9 illustrates an example of where this drape would be located. The patient 27 may be supported on the support member 128 in a face up or face down position. In a face down position, the hole 134 may be used for routing of one or more intubation tubes (not shown) or other medical instruments to the patient 27.

This results in locating the tool support 122 outside the drape 130, in the surgical field. This is also true for any other attendant hardware or assembly components 166 connected thereto, such as a skull clamp 174. For some types of surgical procedures, this draping arrangement may be preferable during surgical or scanning procedures. At least with respect to scanning, this configuration helps to assure that no structure will impede movement of the table extension assembly 126 into the scanning zone.

With this embodiment, i.e., the tool support 122 and the outer stabilization device 166, in this case the skull clamp 174, connected "outboard" of the outer edge of the support member 128, it is also possible to hold the head of the patient with a removably connected, tiltable horseshoe 132 located inboard of the edge of the support plate member 128 (FIGS. 8, 9). FIG. 10 shows the headrest 132 tilted relative to the support member 128. With the tiltable horseshoe headrest 132, there is a first connection piece 132a which mounts to an inside edge of the opening 134 and a pair of mirror image headrest pieces 132b and 132c (FIG. 8) which connect to each other in a common plane and tilt relative to the piece 132a. This tilting feature gives the surgeon additional versatility in positioning the patient. Both the connector piece 132a and the second headrest pieces 132b and 132c are made of radiolucent material so as to not create artifacts during scanning.

FIGS. 8–10 show outer tooling 166, specifically a skull clamp 174, along with an inner device such as a horseshoe headrest 132 connected to the tool support 122. Preferably the tooling or devices 166 are radiolucent and positively hold the patient in a fixed position relative to the support member 128, so that the patient remains in a desired position during successive surgery and scanning procedures. This is done with the inboard headrest 132 and/or an outer stabilization device 166, to affirmatively hold the patient 27 in a fixed position relative to the support plate 118. This structural capability facilitates convenient positioning of the patient 27 during successive scanning or surgical procedures, thereby enabling the surgeon to conveniently and easily perform follow-up procedures.

While the invention has been illustrated by the description of several embodiments and while the embodiments have been described in considerable detail, there is no intention to restrict nor in any way limit the scope of the appended claims to such detail. Additional advantages and modifications will readily appear to those who are skilled in the art. For example, the support plate 28 may be made of other radiolucent materials and may or may not have a laminated construction. Further, when viewed in a cross-section taken across its width as shown in FIG. 4, the support plate 28 has a curvature; however, the support plate 28 may also be constructed to be flat without such a curvature. Further, while the radiolucent table extension is particularly useful with nonradiolucent operating tables, it may also be used with radiolucent operating tables.

The tool support 54 has been described as an edge strip with a slot 64 having a dovetail shape for receiving and supporting tools; however, as will be appreciated, other configurations of the tool support are anticipated by the invention. For example, the slot 64 may have other shapes. Further, the slot 64 may be replaced by round, square or other shaped holes or coupling elements which are shaped to receive mating elements on tools, thereby supporting and holding the respective tools in a desired position. In addition, the tool support 54 may be a strip extending along the edge of the periphery of the plate 28 without the slot 64 but providing a hard surface for clamping purposes, for example, for using C-clamps to secure tools to the strip. While the tool support 54 is described and illustrated as having a slot 58 for receiving an edge of the plate 28, the tool support 54 can be attached to the plate 28 in other ways. For example, the slot 54 may be on the upper or lower surfaces of the plate 28, or the tool support 54 can be attached to the upper or lower surfaces, or the edge, of the plate 28. In addition, even though the tool support 54 has been described as being made from a radiolucent material, under some circumstances, for example, if the tool support is outside the scan field, the tool support 54 may be made of a nonradiolucent material, for example, metal.

As will be appreciated, the horseshoe-shaped gel filled headrest 32 illustrated and described may have other embodiments. For example, the headrest may be circular or another shape, may be filled with a different material, or may be thicker so that the patient's head is supported fully above the upper surface of the support plate 28. The headrest 132 shown in FIGS. 8–10 represents only one of these possible variations. Further, the opening 34 may have other configurations. For example, the opening 34 may be replaced by, or supplemented by, one or a plurality of holes of any shape for various purposes, for example, ventilating the patient, access for tubes and other equipment, drainage, or openings through which the patient can see or the patient's eyes can be seen. As will be appreciated, separate inserts or built-in hole covers may be used to fill or cap the holes when they are not being used.

As will be appreciated, the aligning tab 124 may be located on the scanner 20, and the slot 126 located on the table 22. In addition, other alignment devices and procedures may be used. For example, the scanner 20 may have a built-in aligning system or the imaging system may be used to align the table 22 to the scanner 20.

Therefore, the invention in its broadest aspects is not limited to the specific details shown and described. Consequently, departures may be made from the details described herein without departing from the spirit and scope of the claims which follow.

What is claimed is:

1. In combination, the invention comprising:
   a portable scanning machine having a toroidal shaped scanning zone and adapted to take scans in the scanning zone;
   an imaging system operatively connected to the scanning machine and adapted to store images representative of scans of the scanning zone taken by the scanning machine;
   a patient table having an upper support surface, the patient table and upper support surface including a radiolucent table extension adapted to support a head and upper torso of a patient residing in a prone position on the upper support surface, the radiolucent table extension being sized to be received within the scanning zone, the patient table and the radiolucent table extension being movable relative to the scanning machine to locate the radiolucent table extension within the scanning zone, and the radiolucent table extension including at least one of the following:
      an opening located inboard of an outer edge of the table extension; and
      a radiolucent tool support located along the edge of the table extension and holding a radiolucent head clamp adapted to securely hold the head of the patient in a fixed position relative to the table extension, thereby to assure the accuracy of scans taken of the patient by the scanning machine and subsequently stored in the imaging system.

2. The invention of claim 1 further comprising:
   a radiolucent headrest located inboard of the outer end of the table extension and adjacent the opening.

3. A support assembly for use with a scanning machine comprising:
   a table;
   a radiolucent member having a first end adapted to be attached to one end of the table, opposed lateral edges, a distal end, an opening located inboard of the distal end, and a patient supporting surface having a periphery formed by the lateral edges and the first and distal ends of the radiolucent member, the patient supporting surface providing subjacent contact and support for an upper torso of a patient; and a radiolucent tool support extending along a portion of the periphery of the patient supporting surface, the tool support adapted to receive and support medical instruments.

4. The support assembly of claim 3 further comprising:

a radiolucent headrest located inboard of the outer end of the table extension and adjacent the opening.

5. The support assembly of claim 4 wherein the opening is oval-shaped and the radiolucent headrest partially surrounds the oval-shaped opening.

6. A support assembly for use with a scanning machine comprising:

a table;

a radiolucent member having a first end adapted to be attached to one end of the table, opposed lateral edges, a distal end, an opening located inboard of the distal end, and a patient supporting surface extending between the lateral edges and the first and distal ends of the radiolucent member, the patient supporting surface providing subjacent contact and support for an upper torso and head of a patient; and a radiolucent patient stabilization device located adjacent the distal end of the radiolucent member, the patient stabilization device adapted to support and hold the head of a patient in a desired position relative to the radiolucent member.

7. The support assembly of claim 6 wherein the patient stabilization device comprises:

a radiolucent skull clamp mounted to a radiolucent tool support which extends along a periphery of the radiolucent member.

8. The support assembly of claim 6 wherein the patient stabilization device comprises:

a radiolucent horseshoe headrest located near the opening.

9. The support assembly of claim 8 wherein the radiolucent headrest is located inboard of the distal end.

10. A table extension attachable to a table for use with a scanning machine comprising:

a radiolucent member having a first end adapted to be attached to one end of a table, opposed lateral edges, a distal end, an opening located inboard of the distal end, and a patient supporting surface extending between the lateral edges and the first and distal ends of the radiolucent member, the patient supporting surface providing cantilevered subjacent contact and support for an upper torso and head of a patient, and the distal end being sized to be received within a scanning zone of the scanning machine; and a radiolucent patient stabilization device located adjacent the distal end of the radiolucent member, the radiolucent patient stabilization device adapted to support and hold the head of a patient in a desired position relative to the radiolucent member.

11. The support assembly of claim 10 wherein the patient stabilization device comprises:

a radiolucent skull clamp mounted to a radiolucent tool support which extends along a periphery of the radiolucent member.

12. The support assembly of claim 10 wherein the patient stabilization device comprises:

a radiolucent horseshoe headrest located near the opening.

13. The support assembly of claim 12 wherein the radiolucent headrest is located inboard of the distal end.

* * * * *